United States Patent
Martel et al.

[11] Patent Number: 5,498,234
[45] Date of Patent: *Mar. 12, 1996

[54] HAND AND ARM SUPPORT

[75] Inventors: Stephen J. Martel; Scott A. Clark, both of Cornwall; Susan Hannan, Cornwall-on-Hudson, all of N.Y.

[73] Assignee: American Orthopedic Appliance Group, Inc., Cornwall, N.Y.

[*] Notice: The term of this patent shall not extend beyond the expiration date of Pat. No. 5,370,606.

[21] Appl. No.: 307,255

[22] Filed: Sep. 16, 1994

Related U.S. Application Data

[63] Continuation-in-part of Ser. No. 131,027, Oct. 4, 1993, Pat. No. 5,370,606, which is a continuation of Ser. No. 928,134, Aug. 11, 1992, abandoned, which is a continuation of Ser. No. 708,355, May 31, 1991, abandoned.

[51] Int. Cl.⁶ ..................................................... A61F 5/00
[52] U.S. Cl. .............................. 602/64; 602/21; 2/161.1
[58] Field of Search .................................. 602/5, 21, 64; 2/16, 161.1–161.5, 162, 167, 160

[56] References Cited

U.S. PATENT DOCUMENTS

| | | |
|---|---|---|
| 2,314,545 | 3/1943 | Lindfelt . |
| 3,597,765 | 8/1971 | Stanton . |
| 4,183,100 | 1/1980 | DeMarco . |
| 4,330,120 | 5/1982 | Netti ........................................ 2/160 X |
| 4,519,097 | 5/1985 | Chappel, Jr. et al. . |
| 4,709,694 | 12/1987 | O'Connell . |
| 4,738,447 | 4/1988 | Brown . |
| 4,781,178 | 11/1988 | Gordon . |
| 4,843,651 | 7/1989 | Grama et al. . |
| 4,850,341 | 7/1989 | Fabry et al. . |
| 4,905,321 | 3/1990 | Walunga . |
| 4,958,384 | 9/1990 | McCrane . |
| 4,961,418 | 10/1990 | McLaurin-Smith . |
| 4,964,174 | 10/1990 | Martin . |
| 4,967,419 | 11/1990 | Elliot . |

Primary Examiner—Linda C. Dvorak
Attorney, Agent, or Firm—Cooper & Dunham

[57] ABSTRACT

The present invention provides a hand and arm support including a glove body, a front edge, and a rear edge. The front edge includes a plurality of spaced finger holes, while the rear edge defines an opening for a hand. The glove body is made from a thin lightweight elastic spandex material. The hand and arm support optionally includes finger extensions for covering portions of a wearer's fingers, and a forearm extension for covering portions of the wearer's wrist and forearm.

18 Claims, 3 Drawing Sheets

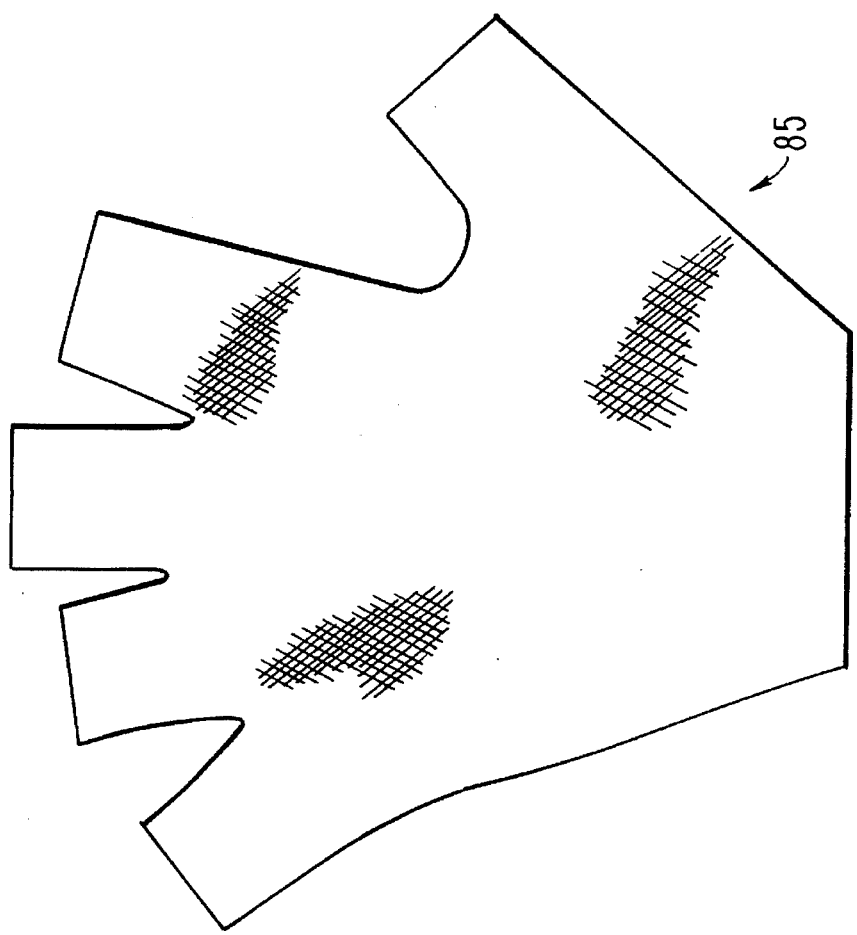
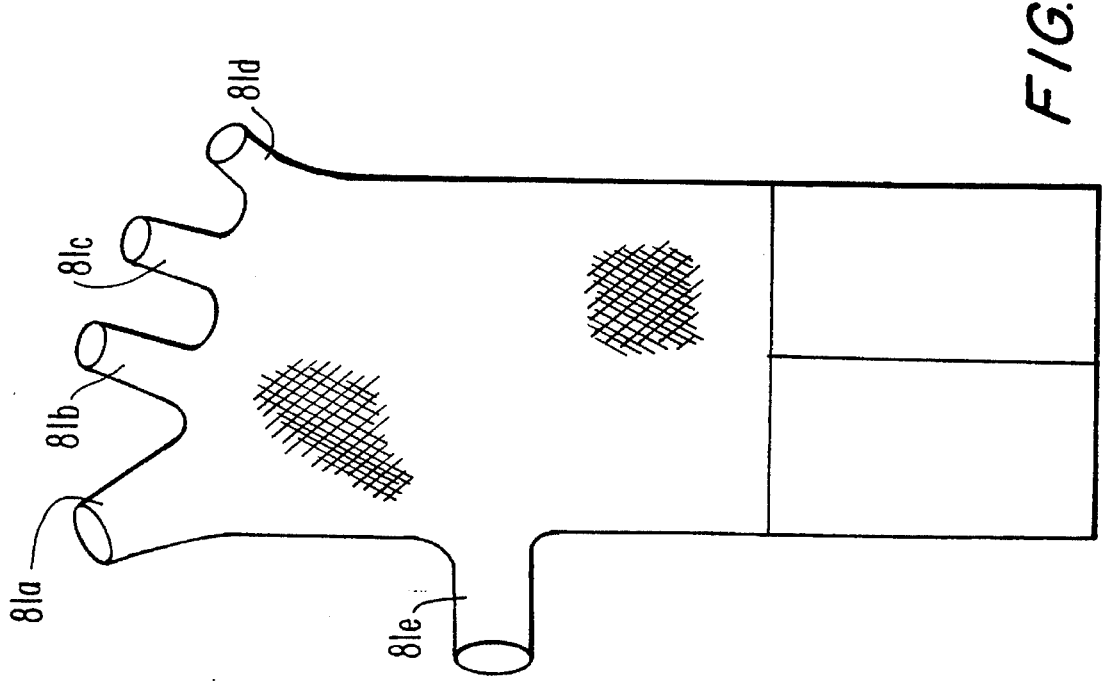
FIG. 7
FIG. 8

HAND AND ARM SUPPORT

CROSS-REFERENCE

This is a continuation-in-part of U.S. patent application Ser. No. 08/131,027, filed Oct. 4, 1993, now U.S. Pat. No. 5,370,606, which in turn is continuation of U.S. patent application Ser. No. 07/928,134, filed Aug. 11, 1992, now abandoned, which in turn is continuation of U.S. patent application No. 07/708,355, filed May 31, 1991, now abandoned.

BACKGROUND OF THE INVENTION

This invention relates to a hand and arm support made of thin, lightweight elastic material for reducing or preventing the effects of ailments such as tendinitis, arthritis and Carpal Tunnel Syndrome, as well as cramping and fatigue.

Many workers perform repetitive hand movements for extended lengths of time, for example, stitchers, typists, assemblers and machine operators. Continuous, repetitive movements associated with these tasks may cause stress in the muscles, nerves and tendons of the hand, fingers, wrist and forearm. This resulting stress can possibly lead to injury and disability. One common injury associated with the stress of repetitive manual tasks is Carpal Tunnel Syndrome, which involves the damage to the nerves and related tissues located in the wrist.

Several hand protectors have been proposed to prevent or reduce the effects of ailments such as Carpal Tunnel Syndrome. According to the patentee of U.S. Pat. No. 4,850,341 (Fabry et al.), a glove can he made of a pliable, sturdy, inelastic such as leather, and includes an elastic panel over the back of the glove to provide a secure fit. The patentee states that the glove also includes a pad secured to the glove body and extending from the wrist opening of the glove across the palm.

U.S. Pat. No. 4,531,241 (Berger) appears to describe a hand glove for use with vibrating machinery to absorb the vibration which may affect the wearer's hand. The patentee states that the hand glove is rectangular in shape and designed to wrap around the wearer's hand, with the hand glove terminating below the fingers. It appears to have a pad on the outside of the glove, in the palm area, made of leather to absorb some of the vibration from the tool being used. The hand glove also has an inside cushion adjacent the wearer's palm. The inside cushion is made of rubber, for example, to rest against the wearer's palm and further absorb the vibration of the tool.

The previous attempts provide gloves which may not alleviate the stress induced by repeated hand movements, and may not allow enough freedom of movement to enable a worker to perform some common manufacturing tasks comfortably and for extended periods of time.

SUMMARY OF THE INVENTION

It is therefore a principal object of the present invention to provide a thin, lightweight, flexible and breathable glove which can be worn to eliminate or reduce stress and injury selectively in the hand, fingers, wrist and forearm resulting from the precise and continuous movements associated with the performance of repetitive manual tasks.

The present invention provides a hand and arm support including a glove body, a front edge, and a rear edge. The front edge includes a plurality of spaced finger holes, while the rear edge defines an opening for a hand. The glove body is made from a thin lightweight elastic spandex material.

The hand and arm support may include finger extensions for covering a portion of the wearer's fingers. The extensions provide additional support for the finger joints, and simultaneously protect the fingers and joints from abrasions associated with the manual task being performed.

The hand and arm support also may include a forearm extension, selectively extendable to cover the wearer's wrist, or to cover a portion of the wearer's forearm. The forearm extension provides additional support for the nerves and tendons in the wearer's wrist and forearm, and protects the wearer from abrasions.

The elastic nature of the hand and arm support provides a snug fit around the wearer's hand and arm, thereby supporting the muscles, tendons, and ligaments of the fingers, hand, wrist and forearm to help prevent injuries such as Carpal Tunnel Syndrome. At the same time, the elastic hand and arm support allows the wearer to maintain a normal range of motions, while causing minimal interference with the performance of manual tasks.

In another embodiment, the invention provides a hand and arm support made from a layered material. The layered material includes padding to protect the wearer from vibration. The hand and arm support includes a glove body, a front edge and a rear edge. The front edge includes a plurality of spaced finger holes, while the rear edge defines an opening for a hand. The glove body is made from a thin, lightweight, flexible elastic material, which includes two outer layers of elastic spandex material surrounding an inner layer of padding.

These and other objects, features and advantages of the present invention will be apparent upon reading the following detailed description of the preferred embodiments in conjunction with the accompanying drawings.

BRIEF DESCRIPTION OF THE DRAWINGS

FIG. 7 is a top view of a hand and arm support including finger extensions, according to an embodiment of the present invention.

FIG. 8 is a top view of a blank form used to manufacture the glove.

DETAILED DESCRIPTION OF PREFERRED EMBODIMENTS

Figure 1:
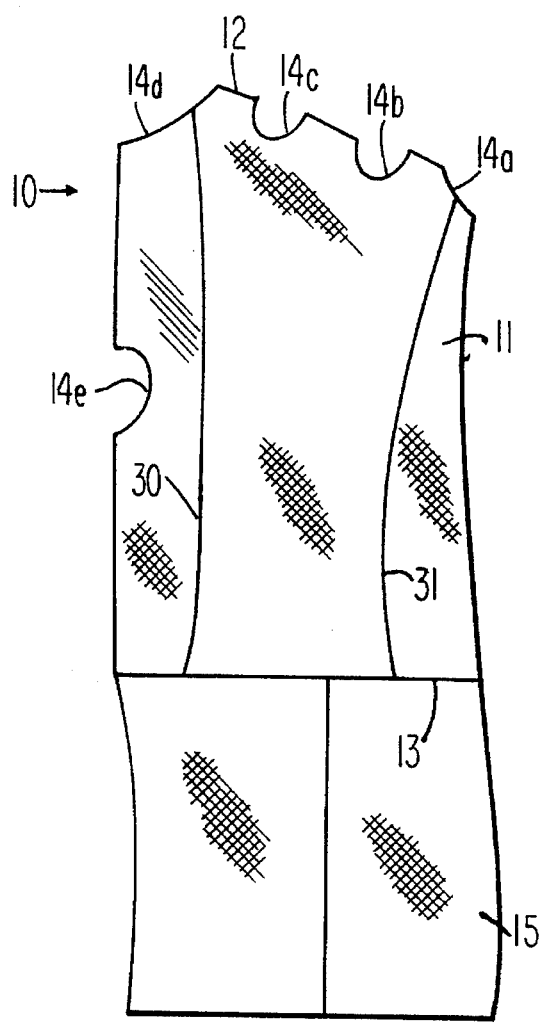
FIG. 1 is a top view of a hand and arm support according to a first embodiment of the present invention.

As shown in FIG. 1, the hand and arm support 10 of the present invention includes a glove body 11 with front edge 12 and rear edge 13. A plurality of finger holes 14a–14e, corresponding to the fingers and thumb of a wearer, are spaced along the front edge 12. Rear edge 13 defines an opening for the wearer's hand. The hand and arm support 10 also preferably includes a cylindrical wrist cuff or forearm extension 15 which is attached to, or forms a part of, rear edge 13.

In a first embodiment, the glove body 11 and wrist cuff or forearm extension 15 are made of a thin, lightweight elastic spandex and nylon material to provide support for the muscles and tendons of the hand, wrist and forearm while allowing the wearer maximum flexibility for performing repetitive, precise hand and arm movements. Preferably, the elastic spandex material is made from a combination of about 10% to about 30% (preferably about 15% to about 25%) spandex and about 70% to about 90% (preferably about 75% to about 85%) nylon and has a thickness in the range of about 0.023 to about 0.027 inches. Of course, various similar materials can be used, from various vendors, and selection maybe made taking into consideration the end use, desired support and thickness. The presently preferred material is available from Darlington Mills, located in Westerly, R.I., as style no. 2571, and contains about 20% spandex and about 80% nylon. Other preferred materials are available from Liberty Fabrics of Gordonville, Va., as style no. 97774; Charbert Fabrics of Alton, R.I., as style nos. 34926 and 34798; and Milliken of Spartansburg, S.C., as style nos. 9122 and 2410.

The use of spandex material gives the glove a flexibility of about 75% in the direction of the weave of the material and about 50% against the weave of the material. Preferably, the weave of the spandex material in the glove body runs from the front edge 12 to the rear edge 13, as indicated by arrow A in FIG. 2. The weave of the material in the wrist cuff or forearm extension 15 preferably runs circumferentially around the cuff 15, that is, around the wrist or forearm, as indicated by arrow B in FIGS. 2 and 5.

Figure 4:
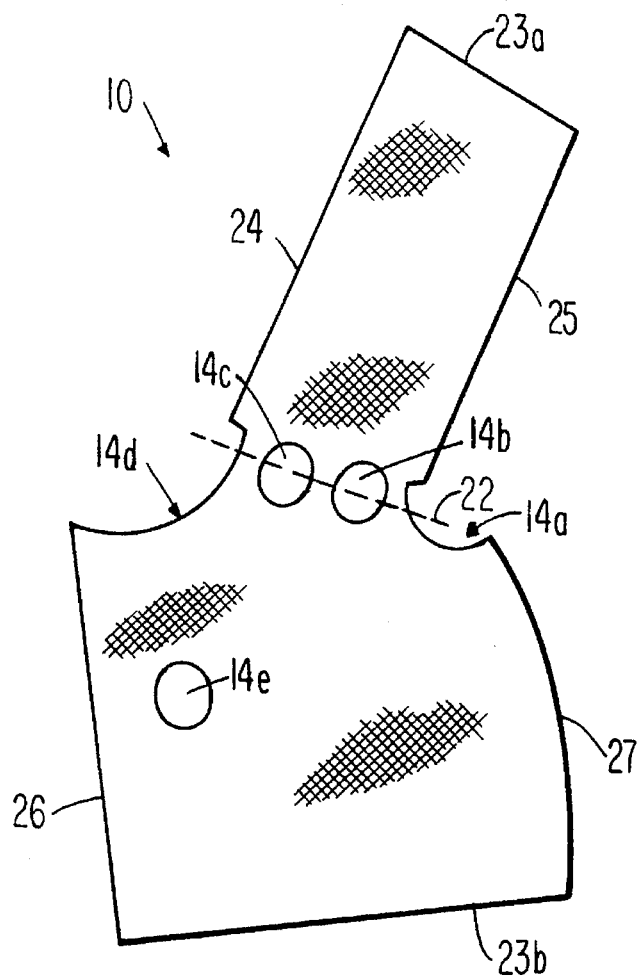
FIG. 4 is a top view of a blank for fabricating the hand and arm support of the present invention.

The glove body 11 is manufactured by cutting a blank form of the preferred material, as shown in FIG. 4, with finger holes 14b, 14c and 14e cut out of the blank. Dashed line 22 corresponds to front edge 12 and edges 23a and 23b correspond to rear edge 13. The blank is folded along dashed line 22 so that edges 23a and 23b are aligned. Edge 24 is sewn to edge 26 to form seam 30 and finger hole 14d, shown in FIG. 1. Similarly, edge 25 is sewn to edge 27 to form seam 31 and finger hole 14a.

Figures 5, 6:
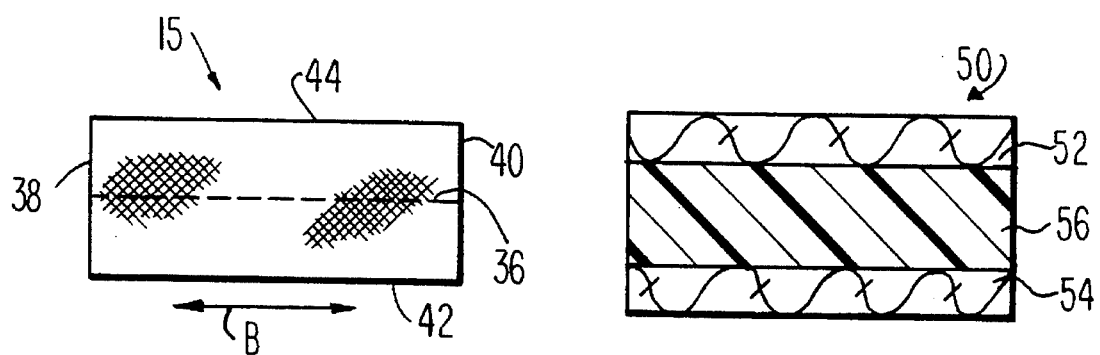
FIG. 5 is a top view of a blank for fabricating a wrist cuff or forearm extension which forms a part of the hand and arm support shown in FIG. 1.
FIG. 6 is a sectional view of the material used in fabricating a hand and arm support according to a second embodiment of the present invention.

The wrist cuff or forearm extension 15 is preferably made from a rectangular piece of material, as shown in FIG. 5. The material is folded in half, along dashed line 36, to form a 2-ply strip to provide extra support for the wearer's wrist and forearm. End 38 is sewn to end 40, and edges 42 and 44 together are sewn to rear edge 13. The length of ends 38 and 40 can be selected so that the wrist cuff or forearm extension 15 provides support and protection for selected portions of the wearer's forearm. For example, the extension may cover only the wearer's wrist, or may extend to a midpoint between the wearer's wrist and elbow.

Alternatively, the wrist cuff or forearm extension 15 can be adapted specially for the desired use to provide the desired combination of support and freedom of movement. For example, the wrist cuff or forearm extension can be formed of a multiple weave of the elastic spandex material for enhanced thickness, or of a single weave of material composed of a lower percentage of spandex. In either case, the wrist cuff or forearm extension is attached to the glove body in the same manner as described above. As another alternative, the wrist cuff or forearm extension may be woven directly from the edges 23a and 23b of the glove body blank in any desired weave or available thickness.

Still referring to FIG. 4, the hand and arm support 10 can be made for the left hand or the right hand by folding the blank either forward or backward along dashed line 22. In addition, the hand and arm support can be made in different sizes simply by cutting blanks of various sizes. For example, a support corresponding to small, medium and large sizes can be made by adjusting the size of the glove blank for the appropriate end size. Each size support is cut and sewn in essentially the same way.

The hand and arm support optionally may include finger extensions, as shown in FIG. 7. In this embodiment, the glove is manufactured by preparing two blank forms of the preferred material, one of which is shown as 85 in FIG. 8. The forms are positioned in an opposing relationship and the edges are sewn together, leaving openings at each fingertip and at the wrist. Preferably, the finger extensions do not cover the entire finger. Thus, at least the wearer's fingertips remain exposed so the wearer does not lose sensitivity of touch, and precise movements are facilitated. A wrist cuff or forearm extension is attached in the same manner as in the fingerless embodiment.

Similarly to the wrist cuff or forearm extension, the finger extensions can be manufactured to provide any desired amount of support relative to the glove body. For example, the finger extensions can be made from a single- or double-ply of the same material as the glove body, a multiple weave of material having similar characteristics as the glove body, or a single or multiple weave of material having different characteristics as the glove body. In such a case, the finger extensions can be separately formed and sewn onto a fingerless glove body.

In use, the hand and arm support 10 is slipped on the hand of the wearer much as an ordinary glove, so that the seams are on the inside of the support 10 against the top of the wearer's hand. If the seams 30, 31 tend to irritate the wearer's skin, the support 10 also can be turned inside out, so that the seams 30, 31 are on the outside of the support 10. This is particularly helpful for wearers who suffer from edema, or other swelling conditions, in their hands.

The support 10 fits snugly around the wearer's fingers, hand and wrist or forearm, so that it supports without being constricting or uncomfortable. As the wearer's hands, fingers and arm move, the hand and arm support 10 continuously supports the structures of the hand and forearm without discomfort and without interfering with precise and repetitive movements. With regular use, the hand and arm support 10 can help prevent cramping and fatigue, and can help avoid the onset, or alleviate the symptoms, of ailments such as tendinitis, arthritis and Carpal Tunnel Syndrome.

In a second embodiment of the present invention (not separately shown), the glove body 11 and wrist cuff or forearm extension 15 are made of a padded elastic material to provide flexibility and support for the muscles and tendons of the hand and arm, similar to the first embodiment, but to protect the hand and arm from shock and to prevent inflammation when the wearer operates vibrating machinery. A cross-section of this material is shown in FIG. 6.

As stated above, the second embodiment of the hand and arm support resembles the embodiment of FIGS. 1–5, but additionally and advantageously provides integral padding to help protect the wearer from vibrations from electric hand tools commonly employed on assembly lines, such as electric cutting tools, drills, power wrenches, pneumatic tools and the like. As shown in FIG. 6, the support in accordance with the second embodiment is made of a layered material 50 which includes two outer layers of elastic spandex material 52 and 54. The outer layers 52 and 54 preferably are made from a combination of about 10% to about 30% (preferably about 15% to about 25%) spandex and about 70% to about 90% (preferably about 75% to about 85%) nylon, as in the first embodiment. Outer layer 52 has a thickness in the range of about 0.016 to about 0.020 inches, and inner layer 54 has a thickness in the range of about 0.023 to about 0.027 inches. The material 50 also includes an inner layer of padding 56, such as polyurethane, having a thickness in the range of about 0.017 to about 0.021 inches, making a total thickness of the glove from about 0.056 to about 0.068 inches.

Figure 2:
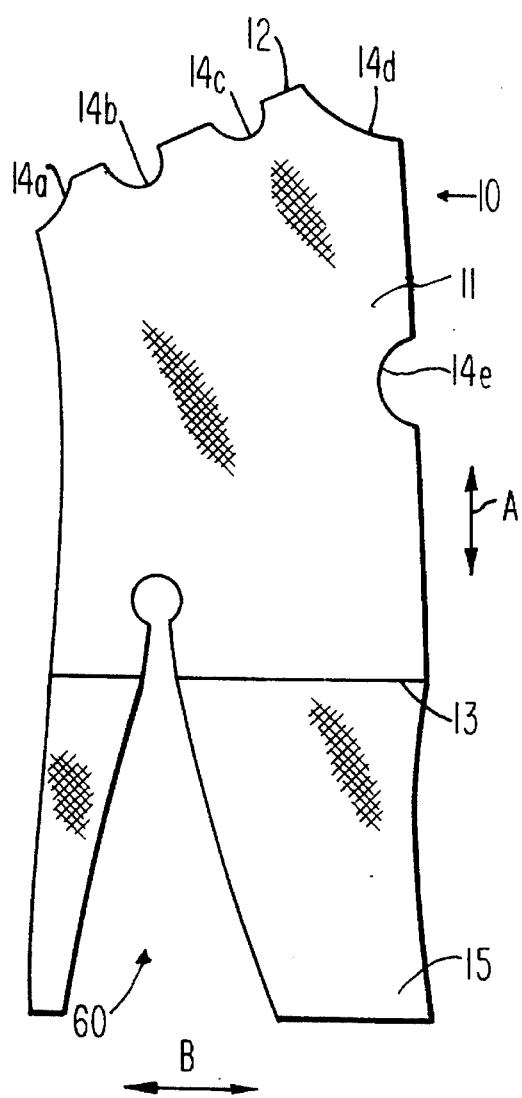
FIG. 2 is a bottom view of the hand and arm support shown in FIG. 1.
Figure 3:
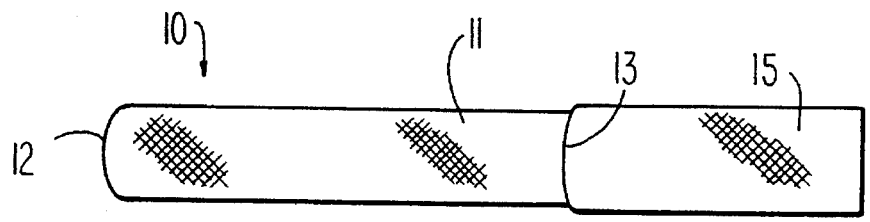
FIG. 3 is a side view of the hand and arm support shown in FIG. 1.

The support according to the second embodiment has an elasticity of about 75% in the direction of the weave of the material, and 65% against the weave, with the weave running in the same directions as in the first embodiment (see FIGS. 2 and 4). The support according to the second embodiment thus stretches somewhat less than the support 10 of the first embodiment because of the increased padding. While the support provides adequate support for the hand structures prone to cramping and fatigue, and likely to be affected by ailments such as tendinitis, arthritis and Carpal Tunnel Syndrome, it advantageously provides increased insulation from shock and vibration for those tasks judged to require such protection. Advantageously, the hand and arm support 10 of the present invention can be adapted and modified for a specific task to provide the correct balance of support and insulation by varying these two parameters through use of various materials. Similar to the first embodiment, the second embodiment may include finger extensions, or a wrist cuff or forearm extension.

The first embodiment of the invention also may include a pocket in the area of the wearer's palm for holding an amount of foam to protect the wearer's hand from vibration, while providing the wearer with the flexibility of the support of the first embodiment. Alternatively, a patch of layered material of the second embodiment may be sewn into the support of the first embodiment in the area of the wearer's palm, or the bottom of the support 10 can be made from the material shown in FIG. 6, with a piece of the material used in the embodiment of FIG. 1 covering the back of the hand.

The hand and arm support 10 of the second embodiment is manufactured in much the same way as the hand and arm support 10 of the first embodiment, that is, by cutting and assembling the hand and arm support from a blank as shown in FIG. 4. However, the wrist cuff or forearm extension 15 used in the second embodiment may be a single layer of material.

The hand and arm support 10 of the present invention can also include fastening means for releasably securing the support to the wearer's hand. Fastening means are particularly helpful in the second embodiment, where the support is less elastic, or where a long forearm extension is used, thus making the support difficult to put on and remove. The hand and arm support 10 also can be provided with a wider opening without sacrificing snugness.

Conventional fastening means can include a vent 60 cut into the glove opening, as shown in FIG. 2. Hook and loop fasteners, often called "Velcro," for example (not shown), can be positioned on the glove opening adjacent the vent so that, when fastened, the hand and arm support will fit tightly around the wearer's wrist or forearm.

Having described preferred embodiments of the invention in detail with reference to the accompanying drawings, it is to be understood that the invention is not limited to those precise embodiments and that many changes and modifications could be effected by one with skill in the art without departing from the spirit and scope of the invention as defined in the appended claims.

What is claimed is:

1. A hand and arm support for prevention and treatment of cramping, fatigue and ailments such as tendinitis, arthritis and Carpal Tunnel Syndrome, consisting essentially of:

a glove body of a material having uniform thickness throughout the glove body and forming a fingerless glove, the glove body having a front edge and a rear edge, the front edge including a plurality of finger holes spaced along the front edge, the rear edge defining an opening for a hand, the glove body made solely from a thin lightweight elastic spandex and nylon material and sized to provide a snug fit around a wearer's hand, the hand and arm support defining a cylindrical forearm extension attached to the rear edge for supplying support to at least a portion of the wearer's forearm.

2. A hand and arm support according to claim 1, wherein the elastic spandex material forming the glove body has an elasticity of about 75% with the weave and 50% against the weave.

3. A hand and arm support according to claim 1, wherein the elastic spandex material forming the glove body is formed of about 10% to about 30% spandex and about 70% to about 90% nylon.

4. A hand and arm support according to claim 1, wherein the elastic spandex material forming the glove body is formed of about 15% to about 25% spandex and about 75% to about 85% nylon.

5. A hand and arm support according to claim 2, wherein the weave of the spandex material forming the glove body runs from the rear edge to the front edge of the hand and arm support.

6. A hand and arm support according to claim 1, wherein the forearm extension is made from the same material as the glove body.

7. A hand and arm support according to claim 1, wherein the forearm extension is adapted to cover the wearer's wrist and at least a portion of the wearer's forearm.

8. A hand and arm support according to claim 1, having finger extensions extending from the glove body.

9. A hand and arm support according to claim 8, wherein the finger extensions are made from the same material as the glove body.

10. A hand and arm support according to claim 8, wherein the finger extensions are adapted to extend at least part way along the wearer's fingers.

11. A hand and arm support for prevention and treatment of cramping, fatigue and ailments such as tendinitis, arthritis and Carpal Tunnel Syndrome, consisting essentially of:

a glove body of a material having uniform thickness throughout the glove body, having a front edge and a rear edge, the front edge including a plurality of finger extensions spaced along the front edge, the rear edge defining an opening for a hand, the glove body made solely from a thin lightweight elastic spandex and nylon material and sized to provide a snug fit around a wearer's hand, the hand and arm support defining a cylindrical forearm extension attached to the rear edge for supplying support to at least a portion of the wearer's forearm.

12. A hand and arm support according to claim 11, wherein the finger extensions are adapted to extend at least part way along the wearer's fingers.

13. A hand and arm support according to claim 11, wherein the finger extensions are of the same material as the glove body and are sized to provide a snug fit around a wearer's fingers.

14. A hand and arm support for prevention and treatment of cramping, fatigue and ailments such as tendinitis, arthritis and Carpal Tunnel Syndrome, consisting essentially of:

a glove body and a forearm extension, both consisting of a material made solely of lightweight elastic spandex and nylon material and having uniform thickness throughout the glove body and the forearm extension, the glove body having a front edge and a rear edge and being formed of a top piece and a bottom piece sewn together along their corresponding edges, the glove body having a plurality of finger holes spaced along the front edge forming a fingerless glove, the forearm extension attached to the rear edge for supplying support to the wearer's wrist, said lightweight elastic spandex and nylon material having a combination of about 10% to about 30% spandex and about 70% to about 90% nylon, an elasticity of about 75% with the weave and 50% against the weave and a thickness ranging from about 0.023 inches to about 0.027 inches and sized to provide a snug fit around the wearer's hand, wherein the glove supports the structures of a hand when the hand performs repetitive tasks.

15. A hand and arm support according to claim 14, wherein the forearm extension is made from a single-ply of the same material as the glove body.

16. A hand and arm support according to claim 14, wherein the forearm extension is made from a double-ply of the same material as the glove body.

17. A hand and arm support according to claim 14, wherein the forearm extension is made from a multiple weave of material having the same properties as the material from which the glove body is formed.

18. A hand and arm support according to claim 1, further comprising an emblem or design formed on the top of the glove body.

* * * * *